United States Patent [19]

Shen et al.

[11] 4,133,673

[45] Jan. 9, 1979

[54] (AMINOPHENYL)MORPHOLINES

[75] Inventors: Kelvin K. Shen, Fountain Valley, Calif.; Wayne S. Belles, Moscow, Id.

[73] Assignee: United States Borax & Chemical Corporation, Los Angeles, Calif.

[21] Appl. No.: 899,955

[22] Filed: Apr. 25, 1978

Related U.S. Application Data

[62] Division of Ser. No. 766,289, Feb. 7, 1977.

[51] Int. Cl.$^2$ .................... C07D 295/06; A01N 9/14
[52] U.S. Cl. ........................................ 71/88; 260/239.7
[58] Field of Search ............................ 544/159; 71/88; 260/239.7

[56] References Cited

U.S. PATENT DOCUMENTS 3,764,624  10/1973  Strong et al. .................. 544/159

*Primary Examiner*—Natalie Trousof
*Assistant Examiner*—R. W. Ramsuer
*Attorney, Agent, or Firm*—James R. Thornton

[57] ABSTRACT

(2-Aminophenyl)morpholine compounds having a haloalkyl, lower alkylsulfonyl, halo-lower alkylsulfonyl, or branched-chain alkyl substituent on the aromatic ring para to the morpholino nitrogen. The compounds are useful as herbicides and may be used as intermediates for making herbicidal compounds.

10 Claims, No Drawings

(AMINOPHENYL)MORPHOLINES

This is a division of application Ser. No. 766,289, filed Feb. 7, 1977.

This invention relates to novel 4-(2-aminophenyl)-morpholine compounds having selected substituents on the benzene ring.

BACKGROUND OF THE INVENTION

The synthesis of certain morpholinoaniline compounds is described by Nair and Adams in the *Journal of the American Chemical Society*, Volume 83, pages 3518-3521 (1961). These compounds are prepared by the catalytic or chemical reduction of the corresponding ortho-nitrophenylmorpholine compound according to the following reaction

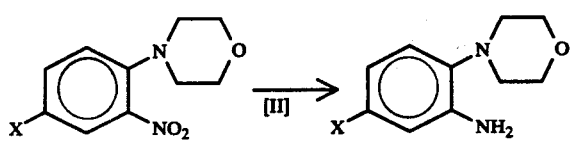

in which X equals hydrogen, chloro, methyl or nitro.

SUMMARY OF THE INVENTION

This invention provides a class of 4-(2-aminophenyl)-morpholine compounds of the following formula

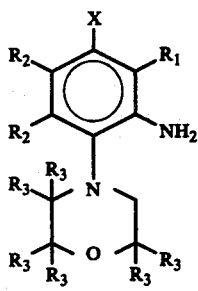

in which X represents halo-lower alkyl, lower alkylsulfonyl, halo-lower alkylsulfonyl, or a branched-chain alkyl group of 3 to about 6 carbon atoms, $R_1$ represents hydrogen, nitro or halo, each $R_2$ is selected from hydrogen, halo, lower alkyl, lower alkoxy, amino and nitro and each $R_3$ is selected from hydrogen and lower alkyl. Such compounds may also be considered 2-morpholinoanilines or o-phenylenediamines. The term "lower alkyl" when used herein is meant to include alkyl groups having up to about six carbon atoms. Examples of groups which may be represented by X include trifluoromethylsulfonyl, trifluoromethyl, isopropyl, tert-butyl, ethylsulfonyl, cyclopropyl, sec-pentyl, sec-butyl, methylsulfonyl, difluoromethylsulfonyl, isoamyl, and the like. Examples of groups which may be represented by $R_1$, $R_2$ and/or $R_3$ include methyl, ethyl, n-propyl, isopropyl, butyl, chloro, bromo, fluoro, methoxy, ethoxy, and the like.

The compounds of this invention are useful as intermediates for the preparation of herbicidal 1,2-morpholinobenzimidazole compounds by means of an oxidative cyclization reaction such as described in the Nair and Adams reference above and in our copending application Ser. No. 671,452 filed Mar. 29, 1976 now U.S. Pat. No. 4,049,422. The compounds are also useful as herbicides, especially when $R_1$, $R_2$ and $R_3$ represent hydrogen. Such compounds comprise a preferred class of this invention, especially when X is a branched chain alkyl group.

The compounds may be prepared by reduction of the corresponding ortho-morpholinonitrobenzene such as with hydrogen in the presence of palladium catalyst. The reaction takes place at room temperature in the presence of a suitable solvent such as alcohols and glycol ethers. The morpholinonitrobenzene compound may be prepared by reaction of morpholine with the corresponding ortho-chloronitrobenzene.

The following examples illustrate the preparation of representative compounds of the invention.

EXAMPLE I 4-(2-Nitro-4-trifluoromethylphenyl)morpholine 4-(2-Nitro-4-trifluoromethylphenyl)morpholine was prepared by reaction of 4-chloro-3-nitrobenzotrifluoride with equimolar amounts of morpholine and triethylamine in monoglyme. The resultant product melts at 37°-39° C.

4-(2-Amino-4-trifluoromethylphenyl)morpholine 4-(2-Nitro-4-trifluoromethylphenyl)morpholine was hydrogenated over palladium on carbon catalyst in monoglyme to give the corresponding 2-amino compound which melts at 126°-129° C.

EXAMPLE II 4-(4-tert-butyl-2-nitrophenyl)morpholine 4-tert-Butyl-2-nitrochlorobenzene (19 g.; 68 mmoles) and morpholine (30 g.; 340 mmoles) were heated at 90° C. for 40 hours. The mixture was then poured into ice water. The yellow solid precipitate was collected by filtration (95% yield) and found to melt at 58°-60° C.

4-(2-Amino-4-tert-butylphenyl)morpholine 4-(4-tert-Butyl-2-nitrophenyl)morpholine (15 g.; 57 mmoles) was dissolved in a mixture of 150 ml. of monoglyme and 150 ml. of methanol. The mixture was then hydrogenated in the presence of 1.4 g. of Pd on carbon catalyst (10%) with an initial pressure of 39 p.s.i. hydrogen. After 3 hours, the resultant mixture was filtered to remove the catalyst and the filtrate evaporated to dryness to give the product (13 g.; 97.8% yield) as tan crystals, m.p. 165°-166° C.

EXAMPLE III 4-(2-Amino-4-isopropylphenyl)morpholine 4-(4-Isopropyl-2-nitrophenyl)morpholine was hydrogenated over Pd-C as described above to give the desired 2-amino derivative, m.p. 123°-125° C.

EXAMPLES IV-XX

The following are other representative compounds of this invention which may be prepared as described above.

IV. 4-(2-amino-4-isopropyl-6-nitrophenyl)morpholine, m.p. 120°-122.5° C.

V. 4-(2-amino-4-tert-butyl-6-nitrophenyl)morpholine, m.p. 161°-163° C.

VI. 4-(2,6-diamino-4-isopropylphenyl)morpholine m.p. 117.5°-119° C.

VII. 4-(2,6-diamino-4-tert-butylphenyl)morpholine, m.p. 128°-129° C.

VIII. 2-methyl-4-(2-amino-4-isopropylphenyl)morpholine, m.p. 50°–52° C.
IX. 4-(2-amino-4-trifluoromethylsulfonylphenyl)morpholine, m.p. 78°–79° C.
X. 4-(2-amino-4-difluoromethylsulfonylphenyl)morpholine, m.p. 160°–161° C.
XI. 4-(2-amino-4-methylsulfonylphenyl)morpholine, m.p. 206°–208° C.
XII. 4-(2,6-diamino-4-trifluoromethylphenyl)morpholine, m.p. 110°–114° C.
XIII. 4-(2-amino-3-chloro-4-isopropylphenyl)morpholine
XIV. 4-(2-amino-5-methoxy-4-trifluoromethylphenyl)morpholine, m.p. 139°–141° C.
XV. 4-(2-amino-4-isoamylphenyl)morpholine
XVI. 4-(2-amino-5-chloro-4-sec.butylphenyl)morpholine
XVII. 4-(2-amino-5-methyl-4-cyclopropylphenyl)morpholine
XVIII. 4-(2-amino-4-isobutyl-6-nitrophenyl)morpholine
XIX. 4-(2-amino-5,6-dichloro-4-isopropylphenyl)morpholine
XX. 4-(2-amino-3-methyl-4-isopropyl-6-nitrophenyl)morpholine
XXI. 4-(2-amino-3-nitro-4-tert.-butylphenyl)morpholine As described above, the compounds are useful as intermediates for preparing herbicidal 1,2-morpholinobenzimidazole compounds, such as by an oxidative cyclization with peroxytrifluoroacetic acid. The reaction can be illustrated as follows.

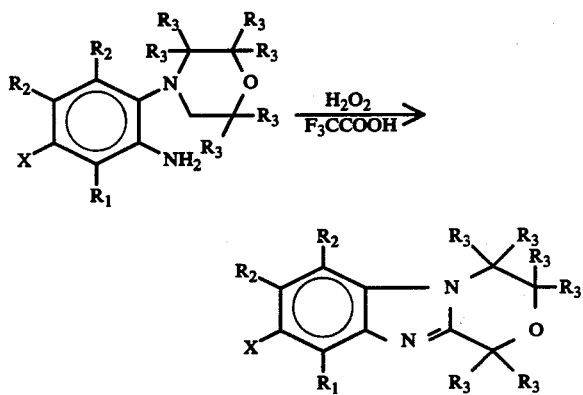

in which X, $R_1$, $R_2$ and $R_3$ have the significance previously assigned. The peroxytrifluoroacetic acid is prepared in situ by using trifluoroacetic acid (or anhydride) and 30% hydrogen peroxide. Solvents such as methylene chloride are generally suitable for the reaction.

In addition to being useful as intermediates for preparing herbicides, a preferred class of compounds of this invention has herbicidal activity. They can be applied as either a pre-emergence or a post-emergence treatment; that is, they can be applied to soil in which the weeds will grow to kill or suppress the emergence of seedlings of undesirable plants or they can be applied to the foliage of the growing plants after emergence from the soil. Thus, the compounds can be used to control the growth of weeds by applying a phytotoxic amount of one or more of the active compounds of this invention to the locus to be protected; that is, soil in which the weeds are growing or will grow or the foliage of the growing plants. When used as a pre-emergence treatment, the compounds may be applied to the soil surface prior to emergence of the weeds or may be incorporated, such as by mixing into the top 1 to 3 inches of the soil prior to planting the crop. When used as a post-emergence treatment, it is preferred that a directed spray be employed, thereby directing the application of the herbicide unto the foliage of the weeds and away from the foliage of the crop plants. Weeds, as used herein, is meant to include any plant growth which is undesirable.

The compounds are especially useful for selectively controlling weeds in the presence of desirable crops such as peanuts, corn, rice, and when applied pre-emergence, soybeans and cotton. The weeds controlled include many of the broadleaf and grassy weeds such as lambsquarter, mustard, pigweed, velvetleaf, cocklebur, barnyard grass, etc.

Generally, an application rate of from about 0.5 to about 15 pounds of one or more of the active compounds per acre is effective in controlling weed growth. Preferably, an application rate in the range of about 1 to 5 pounds per acre is employed.

The following examples illustrate the herbicidal activity of representative compounds of this invention.

EXAMPLE XXII

The compounds to be tested were evaluated as both a pre-emergence and post-emergence treatment. Greenhouse flats were planted to soybeans (SB), velvetleaf (VL), oats (O) and millet (M). The flats were sprayed on the same day as planting with an ethanol solution (sometimes containing added dioxane) of the compound to be tested at a rate of 5 pounds per acre. Another set of flats with the same plants was treated after the plants had emerged and were about 1 inch in height. These flats were also sprayed with the solution of the compound to be tested at a rate of 5 pounds per acre. The flats were kept in the greenhouse and watered when needed. Twenty-one days after treatment, the flats were examined and the plants rated for herbicidal activity on a 0–9 scale in which 0 = no effect, 5 = substantial injury with some kill and 9 = complete kill. Results are shown in Table I. 4-(2-Amino-4-methylphenyl)morpholine, a known compound is included for comparison.

Table I

| Compound | Pre | | | | Post | | | |
|---|---|---|---|---|---|---|---|---|
| (Ex.) | SB | VL | O | M | SB | VL | O | M |
| I | 0 | 7 | 8 | 2 | 0 | 6 | 0 | 0 |
| II | 5 | 9 | 7 | 9 | 8 | 9 | 8 | 9 |
| III | 1 | 9 | 2 | 5 | 1 | 9 | 9 | 9 |
| IV | 0 | 0 | 0 | 0 | 1 | 8 | 0 | 0 |
| XI | 0 | 0 | 0 | 0 | 3 | 8 | 1 | 7 |
| VIII | 0 | 9 | 0 | 2 | 1 | 8 | 0 | 0 |
| 4-(2-Amino-4-methylphenyl)morpholine | 0 | 0 | 0 | 0 | 0 | 2 | 0 | 0 |

EXAMPLE XXIII

Compounds II and III were evaluated as pre-emergence and post-emergence herbicides in greenhouse tests with a broad group of crops and weeds at 1 and 2 pounds per acre. An ethanol solution of the compound to be tested was sprayed on the soil on the same day as planting or on the plants when they were about one inch in height. Twenty-one days after treatment, the plants were rated on a 0 to 9 scale. Where two numbers are used, i.e. 8/4, the first number represents the percent kill and the second number is the injury to the remaining plants, using the following scale.

0 = no effect
1 = <10% injury
2 = 10-40% injury
3 = 40-70% injury
4 = >70% injury
5 = <25% kill
6 = 25-50% kill
7 = 50-75% kill
8 = 75-99% kill
9 = 100% kill The results are given in Tables II and III and are an average of two replicates.

TABLE II

| | Pre-emergence Test | | | |
|---|---|---|---|---|
| | Example II | | Example III | |
| Plants | 1 lb. | 2 lb. | 1 lb. | 2 lb. |
| Corn | 0/1 | 0/1 | 0 | 0 |
| Cotton | 0/2 | 0/2 | 0 | 0 |
| Dry beans | 6/2 | 7/3 | 0 | 0/1 |
| Peanuts | — | — | 0 | 0 |
| Rice | 0/1 | 0/1 | 0 | 0 |
| Soybeans | 0 | 0/1 | 0 | 0 |
| Wheat | 0/2 | 5/2 | 0 | 0 |
| Alfalfa | 9 | 9 | 0 | 5/0 |
| Cocklebur | 5/1 | 9 | 0 | 0 |
| Jimson weed | 6/2 | 6/2 | 0/1 | 7/2 |
| Lambsquarters | 9 | 9 | 5/1 | 8 |
| Morningglory | 0/1 | 0/1 | 0 | 1 |
| Prickly sida | 7/3 | 7/3 | 0 | 0 |
| Pigweed | 8/4 | 9 | 0/2 | 0/1 |
| Sesbania | 0 | 5/1 | 0 | 0 |
| Velvetleaf | 9 | 9 | 0/1 | 7/2 |
| Barnyard grass | 9 | 9 | 0 | 0 |
| Foxtail | 7/3 | 8/2 | 0 | 0 |
| Johnson grass | 7/2 | 8/2 | 0 | 0 |
| Wild oats | 0/1 | 6/2 | 0 | 0 |
| Mustard | 7/3 | 7/4 | 0 | 8/3 |

TABLE II

| | Post-emergence Test | | | |
|---|---|---|---|---|
| | Example II | | Example III | |
| Plants | 1 lb. | 2 lb. | 1 lb. | 2 lb. |
| Corn | 0 | 0/1 | 0 | 0 |
| Cotton | 8/2 | 9 | 8/4 | 9 |
| Dry beans | 9 | 9 | 6/4 | 8/4 |
| Peanuts | 0/1 | 0/1 | 8/2 | 0/1 |
| Rice | 0 | 5/2 | 0 | 0 |
| Soybeans | 0/2 | 9 | 0 | 5/2 |
| Wheat | 0/1 | 7/2 | 0 | 0 |
| Alfalfa | 9 | 9 | 9 | 9 |
| Cocklebur | 9 | 9 | 7/1 | 9 |
| Jimsonweed | 7/2 | 9 | 8/0 | 8/3 |
| Lambsquarters | 9 | 9 | 7/2 | 9 |
| Morningglory | 0/1 | 0/1 | 0 | 0 |
| Mustard | 5/2 | 7/3 | 8/2 | 9 |
| Prickly sida | 8/3 | 8/3 | 0 | 0 |
| Pigweed | 8/1 | 9 | 0 | 8/3 |
| Sesbania | 0/1 | 8/2 | 0 | 9 |
| Velvetleaf | 8/2 | 9 | 0 | 8/0 |
| Barnyard grass | 5/0 | 7/1 | 0 | 0 |
| Foxtail | 0 | 0/1 | 0 | 0 |
| Johnsongrass | 0 | 5/0 | 0 | 0 |
| Wild oats | 0 | 7/2 | 0 | 0 |

Since a relatively small amount of one or more of the active compounds should be uniformly distributed over the area to be treated, they preferably are formulated with conventional herbicide carriers, either liquid or solid. Thus, the compounds can be impregnated on or admixed with a pulverulent solid carrier such as lime, talc, clay, Bentonite, calcium chloride, vermiculite and the like. Alternatively, they can be dissolved or suspended in a liquid carrier such as water, kerosene, alcohols, diesel oil, mineral oil, xylene, benzene, glycols, ketones, and the like. Since the compounds will form water-soluble salts with mineral acids such as HCl, they can be formulated with water.

A surfactant is preferably included to aid in dispersion, emulsification and coverage. The surfactant can be ionic or non-ionic and may be liquid or solid. The use of the term "surfactant" herein is intended to include such compounds commonly referred to as wetting agents, dispersing agents and emulsifying agents. Typical surfactants include the alkylarylsufonates, the fatty alcohol sulfates, sodium salt of naphthalenesulfonic acid, alkylaryl polyether alcohols, long chain quaternary ammonium compounds, sodium salts of petroleum-derived alkylsulfonic acids, polyoxyethylene-sorbitan monolaurate, and the like. These dispersing and wetting agents are sold under numerous trademarks and may either be pure compounds, mixtures of compounds of the same general group, or they can be mixtures of compounds of different classes. Surfactants can also be included in compositions containing a solid inert carrier.

Concentrated compositions containing the active agent which can be subsequently diluted, as with water, to the desired concentration for application to plants and soil are also provided. The advantages of such concentrates are that they are prepared by the manufacturer in a form such that the user need only mix them with a locally available carrier, preferably water, thereby keeping shipping costs to a minimum while providing a product which can be used with a minimum of equipment and effort. Such concentrates may contain from about 5 to about 95 percent by weight of one or more of the active compounds with a carrier or diluent, which may be a liquid or a solid. Liquid carriers which are miscible with the active agent or other liquids in which the compound may be suspended or dispersed, can be used. A surfactant is also generally included to facilitate such dilution or dispersion in water. However, the surfactant itself may comprise the carrier in such concentrates.

The herbicidal compositions can include other beneficial adjuvants, such as humectants, oils and contact agents. Further, other herbicides such as the chlorophenoxyacetic acids, substituted uracils and ureas, triazines, thiocarbamates, carbamates, anilides, amides, and haloalkanoic acids, can be included in the formulation, if desired.

Various changes and modifications of the invention can be made, and, to the extent that such variations incorporate the spirit of this invention, they are intended to be included within the scope of the appended claims.

What is claimed is:
1. A compound of the formula

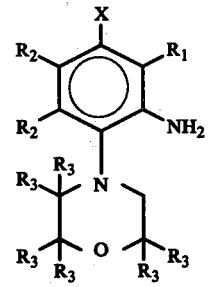

wherein X is selected from lower alkylsulfonyl and halo-lower alkylsulfonyl, $R_1$ represents hydrogen, nitro or halo, each $R_2$ is selected from hydrogen, halo, lower alkyl, lower alkoxy, amino and nitro and each $R_3$ is selected from hydrogen and lower alkyl.

2. A compound according to claim 1 in which $R_1$, $R_2$ and $R_3$ are hydrogen.

3. A mineral acid salt of a compound according to claim 1.

4. A herbicidal composition comprising a herbicidally effective amount of a compound according to claim 2, a surfactant and an inert carrier therefor.

5. The method of controlling undesirable plant growth which comprises applying a phytotoxic amount of a compound according to claim 2 to the locus of said plants.

6. The method according to claim 5 in which said compound is applied to the foliage of said plants.

7. The method according to claim 5 in which said compound is applied at a rate of about 1 to 5 pounds per acre.

8. The compound according to claim 1, 4-(2-amino-4-trifluoromethylsulfonylphenyl)morpholine.

9. The compound according to claim 1, 4-(2-amino-4-difluoromethylsulfonylphenyl)morpholine.

10. The compound according to claim 1, 4-(2-amino-4-methylsulfonylphenyl)morpholine.

* * * * *

UNITED STATES PATENT OFFICE
CERTIFICATE OF CORRECTION

Patent No. 4,133,673    Dated January 9, 1979

Inventor(s) KELVIN K. SHEN & WAYNE S. BELLES

It is certified that error appears in the above-identified patent and that said Letters Patent are hereby corrected as shown below:

In Column 1, Lines 17-24 (formula), delete "$\xrightarrow{[II]}$"

and add -- $\xrightarrow{[H]}$ -- .

In Column 5, Line 32, in Table II, under Pre-Emergence, 2 lb., Johnson grass, delete "8/2" and add -- 8/1 -- .

In Column 5, Line 46, in Table II, under Example III, 2 lb., Alfalfa, delete "9" and add -- 0 -- .

Signed and Sealed this

Twelfth Day of June 1979

[SEAL]

Attest:

RUTH C. MASON
Attesting Officer

DONALD W. BANNER
Commissioner of Patents and Trademarks